United States Patent [19]

Aoki et al.

[11] B 4,014,895

[45] Mar. 29, 1977

[54] METHOD FOR SYNTHESIS OF OPTICALLY ACTIVE THIOLACTONES

[75] Inventors: Yasuhiko Aoki, Toyonaka; Hiroyuki Suzuki, Takarazuka; Hisao Akiyama, Nishinomiya; Shigeru Okano, Kawanishi, all of Japan

[73] Assignee: Sumitomo Chemical Company, Limited, Osaka, Japan

[22] Filed: Dec. 13, 1974

[21] Appl. No.: 532,477

[44] Published under the second Trial Voluntary Protest Program on April 13, 1976 as document No. B 532,477.

Related U.S. Application Data

[62] Division of Ser. No. 372,606, June 22, 1973, Pat. No. 3,876,656.

[30] Foreign Application Priority Data

June 22, 1972 Japan .............................. 47-63032
Mar. 23, 1973 Japan .............................. 48-33912

[52] U.S. Cl. .......................................... 260/309.7
[51] Int. Cl.² ........................................ C07D 49/34
[58] Field of Search ............................... 260/309.7

[56] References Cited

UNITED STATES PATENTS 2,417,326  3/1947  Schnider et al. ............. 260/309.7
2,489,232  11/1949  Goldberg et al. ........... 260/309.7 X

*Primary Examiner*—Ethel G. Love
*Attorney, Agent, or Firm*—Stewart and Kolasch, Ltd.

[57] ABSTRACT

A new method for the production of intermediates in the synthesis of an optically active biotin, which comprises reacting a dicarboxylic acid of the formula:

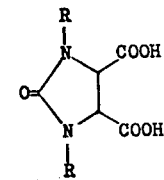

or its reactive derivative with an optically active primary amine, reducing the resulting trione with a metal hydride, hydrolyzing the resultant amide-alcohol and treating the thus produced lactone with a thiolactonating agent to give a thiolactone of the formula:

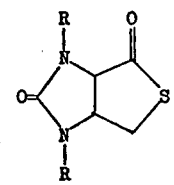

the said trione amide-alcohol being respectively novel and representable by the formulae:

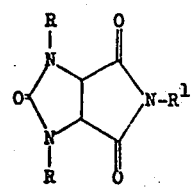

and

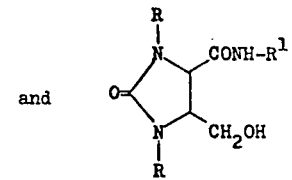

8 Claims, No Drawings

METHOD FOR SYNTHESIS OF OPTICALLY ACTIVE THIOLACTONES

This application is a divisional, of copending application Ser. No. 372,606, filed on June 22, 1973, now U.S. Pat. No. 3,876,656, issued on Apr. 8, 1975.

The present invention relates to intermediates in the synthesis of biotin and their production.

Biotin (also called "Vitamin H") is a valuable substance exerting a growth promoting effect as well as a preventive and therapeutic effect on dermatoses, etc.

For the production of d-biotin, S. A. Harris et al. reported a method wherein dl-biotin is prepared first and then resolved optically by the use of l-arginine [J. Am. Chem. Soc., Vol. 66, 1756 (1944); ibid., Vol. 67, 2096 (1945)]. However, this method is troublesome and involves a great loss of product.

On the other hand, there is known a method developed by M. W. Goldberg et al. wherein d-biotin is produced by the use of an optically active intermediate [U.S. Pat. Nos. 2,489,232, 2,489,233, 2,489,235, 2,489,236, 2,489,238, 2,519,720 and 2,579,682] (this method being hereinafter referred to as "Method (A)"). Thus, Method (A) comprises reacting thiophanium halide with a salt of d-camphorsulfonic acid and fractionally recrystallizing the resulting diastereomeric d-camphorsulfonate to give 1-thiophanium-d-camphorsulfonate as a precursor of d-biotin.

There is also known an improved method proposed by M. Murakami et al. in the production of dl-biotin [Japanese Pat. Nos. 31669/1970, 37775/1970, 37776/1970 and 3580/1971] (this method being hereinafter referred to as "Method (B)"). The improvement is present in the introduction of a 4-carboxybutyl group into the 4-position of dl-1,3-dibenzyl-hexahydrothieno[3,4-d]imidazole-2,4-dione (this compound being hereinafter referred to as "Compound (V)"), which is allowed to react with inexpensively available 1,4-dihalogeno-magnesium-butane, followed by the treatment with carbon dioxide to yield an intermediate of dl-biotin.

As to methods (A) and (B), M. Gerecke et al. reported an improved method wherein d-biotin is produced by the use of optically active Compound (V) obtained from the optical resolution at the early stage of the synthetic route of d-biotin [Helv.Chim.Acta, Vol. 53, 991 (1970)] (this method being hereinafter referred to as "Method (C)"). This method is illustratively shown in the following scheme:

Scheme I

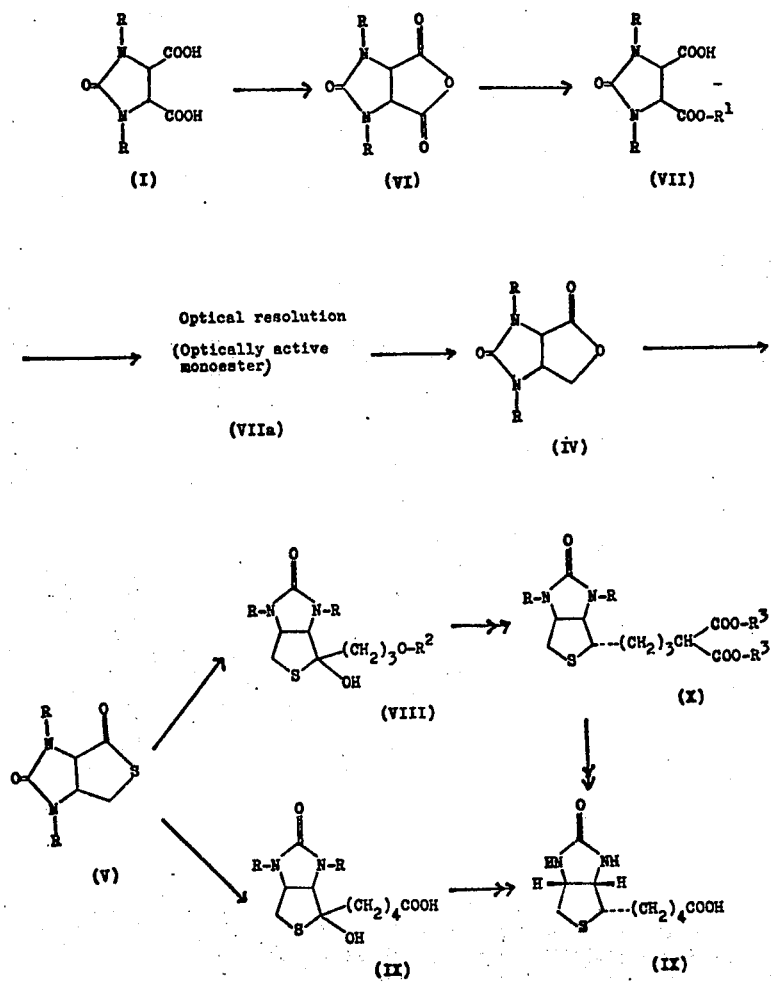

R = benzyl; R$^1$ = cholesteryl or cyclohexyl; R$^2$ = lower alkyl; R$^3$ = lower alkyl.

As seen in the above scheme, the anhydride (VI) produced from the dicarboxylic acid (I) is reacted with an alcohol compound (e.g. cyclohexanol) to give the monoester (VII) of a 2-oxo-imidazolidine-4,5-dicarboxylic acid. The optical resolution of the compound (VII) with ephedrine gives an optically active monoester (VIIa). The compound (VIIa) can be also obtained by optical resolution of the triethylamine salt of the product in the reaction of the compound (VI) with an optically active alcohol compound (e.g. cholesterol). The optically active compound (VIIa) is reduced with lithium borohydride for ring closure to give an optically active lactone (IV), which is then converted into an optically active thiolactone (V), i.e. Compound (V), by treatment with potassium thioacetate in N,N-dimethylformamide or N,N-dimethylacetamide as a thiolactonating agent (i.e. a reagent capable of converting a lactone into a thiolactone). Compound (V) thus obtained is converted to d-biotin according to Method (A) or (B). As mentioned above, an improvemennt is found in Method (C) compared with Methods (A) and (B) with respect to producing an optically active intermediate through optical resolution at the early stage of a synthetic route for d-biotin. However, this Method (C) has a defect that an expensive optically active compound such as ephedrine or cholesterol has to be used. Moreover, it is also defective that the anhydride of dicarboxylic acid (VI) has to be isolated as an intermediate, and an inconvenient agent such as lithium borohydride or potassium thioacetate has to be employed. Thus, Method (C) does not seem to be an industrially satisfactory process.

As the result of an extensive study, there has now been completed an improved process for production of d-biotin which can overcome the defects as seen in the said known methods, particularly in Method (C), and afford readily and economically the lactone (IV) and the thiolactone (V) in an optically active form at a good yield and a high purity.

The process of this invention is illustratively shown in the following scheme: II

Scheme II

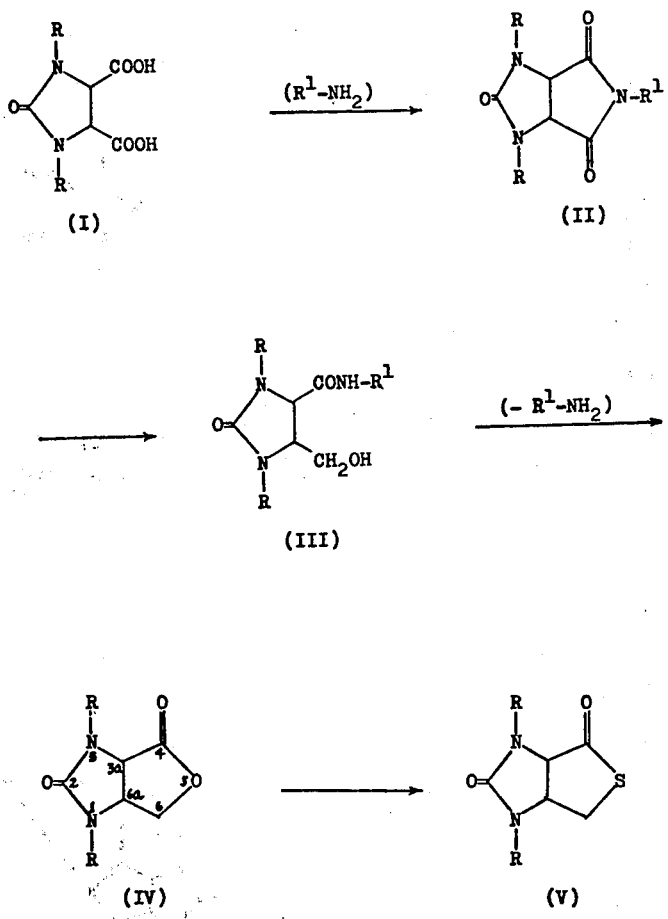

R = benzyl; R$^1$ = optically active primary amine residue.

Thus, the process of this invention comprises reacting the dicarboxylic acid (I) or its derivative with an optically active primary amine (Step [1]), reducing the resulting trione (II) with a metal hydride (Step [2]), hydrolyzing the resultant amide-alcohol (III) (Step [3]) and treating the thus produced lactone (IV) with a thiolactonating agent to give the corresponding thiolactone (V) (Step [4]).

In the above process, the reduction of the trione (II) with a metal hydride proceeds stereo-selectively or stereo-specifically to give the amide-alcohol (III) in an optically active form. Hydrolysis of the resultant amide-alcohol (III) can also afford the lactone (IV) in an optically active form.

More in details, the reduction of the trione (II) is expected to afford two diasteromers but, in actuality, one enantiomer of them is produced predominantly or, in some cases, exclusively. For instance, the reduction of the trione (II: R = benzyl; $R^1$ = (R)-1-phenethylamine residue) with sodium borohydride in 95 % ethanol gives the corresponding amide-alcohol (III) in an optical yield (asymmetric yield) of about 30 %, and the fractional recrystallization of the latter from aqueous isopropanol affords an optically pure product in a yield of about 50 to 55 % based on the trione (II). Hydrolysis of the resulting optically active amide-alcohol (III: R = benzyl; $R^1$ = (R)-1-phenethylamine residue) with an acid gives quantitatively the corresponding lactone (IV) in an optically pure form. Further, for instance, the reduction of the trione (II: R = benzyl; $R^1$ = (1S,2S)-(+)-threo-1-(p-nitrophenyl)-2-amino-1,3-propanediol residue) with sodium borohydride in 95 % ethanol gives the corresponding amide-alcohol (III) in an optical yield of about 75 to 80 %, and the fractional recrystallization from isopropanol affords an optically pure product in a yield of about 60 to 65 %. Hydrolysis of the resultant optically active amide-alcohol (III: R = benzyl; $R^1$ = (1S,2S)-(+)-threo-1-(p-nitrophenyl)-2-amino-1,3-propanediol residue) with hydrochloric acid gives the corresponding lactone (IV) quantitatively in an optically pure form with the simultaneous recovery of (1S,2S)-(+)-threo-1-(p-nitrophenyl)-2-amino-1,3-propanediol hydrochloride in a high yield, e.g. more than 90 %.

In the thiolactonation, it may be noted that the conversion of the lactone (IV) into the thiolactone (V) can be accomplished in a good yield with ease by the use of a thiolactonating agent such as the combination of an alkali metal hydrosulfide (e.g. sodium hydrosulfide, potassium hydrosulfide) and carbon disulfide or the combination of phosphorus pentasulfide and imidazole. It may be also noted that the lactone (IV) in an optically active form can be converted into the corresponding thiolactone (V) without epimerization at the 3a-position. It is advantageous is that such readily available and inexpensive reagents as mentioned above can be employed as the thiolactonating agent.

As understood from the above descriptions, the process of this invention utilizes the so-called "asymmetric synthesis" and makes it possible to produce the lactone (IV) and the thiolactone (V) readily in good yields without adopting any tedious and troublesome step for optical resolution. Since these compounds are known to be important key intermediates in the synthesis of biotin and its related compounds such as α-dehydrobiotin and α-methyl-desthio-biotin, the present invention provides an advantageous process for producing those compounds in an optically active form.

In Step [1], the dicarboxylic acid (I) or its reactive derivative such as the acid anhydride, ester or halide is reacted with an optically active primary amine such as (R)-1-phenethylamine or (1S,2S)-(+)-threo-1-(p-nitrophenyl)-2-amino-1,3-propanediol in the presence or absence of an inert solvent such as an aromatic hydrocarbon (e.g. benzene, toluene) or an ether (e.g. dioxane), favorably in the presence of a basic substance such as a tertiary amine (e.g. pyridine, triethylamine, n-tributylamine). When no solvent is present, the reaction is performed while fusing a mixture of the reactants. Sometimes, a favorable result can be obtained by carrying out the reaction in an organic solvent until an intermediary compound of the formula:

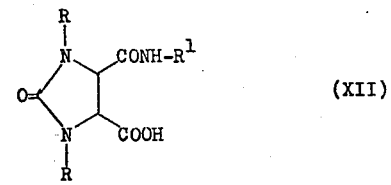

(XII)

wherein R and $R^1$ are each as defined above is formed and, after removal of the solvent, fusing the residue.

The reaction may be executed at a wide range of temperature and usually at the boiling temperature of the solvent as employed or the refluxing temperature of the reaction mixture. It is particularly preferred to perform the reaction while azeotropically eliminating the by-produced water from the reaction system. The reaction period of time depends on the kinds of the reactants and the solvent, the reaction temperature and so on. When effected under reflux, the reaction is usually completed in 1 to 20 hours.

The recovery of the produced trione (II) from the reaction mixture may be effected in a per se conventional procedure. For instance, the reaction mixture is cooled and the precipitated crystals are collected by filtration. When the produced trione (II) is not readily precipitated on cooling, the solvent is removed from the reaction mixture and the residue is recrystallized from a suitable solvent. The yield of the product in this step is almost quantitative.

In [2], the reduction of the trione (II) with a metal hydride is usually carried out in an inert solvent such as an alcohol (e.g. methanol, ethanol, isopropanol), an ether (e.g. diethyl ether, tetrahydrofuran, dioxane), an aromatic amine (e.g. pyridine, picoline), an amide (e.g. N,N-dimethylformamide, N,N-dimethylacetamide), water or a mixture of water and the above mentioned solvents at a temperature within the range between −60°C and the boiling point of the solvent as used, preferably at room temperature. It is sometimes favored that an organic tertiary amine (e.g. triethylamine, N-methylpiperidine, N-methylmorpholine), an inorganic base (e.g. sodium hydroxide, potassium hydroxide) or an inorganic salt (e.g. sodium carbonate, potassium carbonate, dibasic sodium phosphate, tribasic sodium phosphate) is present in the reaction system.

As the metal hydride, there may be used, for instance, an alkali borohydride (e.g. lithium borohydride, sodium borohydride, potassium borohydride, lithium borohydride, calcium borohydride) the combination of an alkali borohydride (e.g. sodium borohydride) and aluminum chloride, an alkali alkoxyborohydride (e.g. sodium trimethoxyborohydride), an alkali alkoxyaluminohydride (e.g. sodium ethoxyaluminohydride, lithium ethoxyaluminohydride), etc. There may be also used diborane generated by the reaction of the above mentioned metal hydride such as sodium borohydride with boron trifluoride.

When the reduction is carried out at a relatively high temperature, for instance, between 0°C and the boiling point of the solvent as employed, the amide-alcohol (III) is produced in a good yield. On the other hand, with the execution of the reduction at a relatively low temperature, e.g. between −60 and 10°C, there is produced in a good yield a dione of the formula:

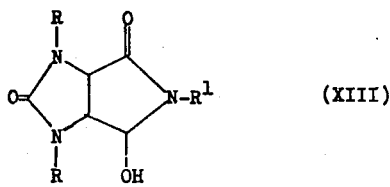 (XIII)

wherein R and $R^1$ are each as defined above. This dione (XIII) is readily converted into the amide-alcohol in a good yield by treating with the metal hydride as mentioned above at a temperature from 0°C to the boiling point of the solvent as employed, usually at room temperature.

The recovery of the amide-alcohol (III) or the dione (XIII) from the reaction mixture can be readily accomplished by a per se conventional procedure, for instance, cooling the reaction mixture below room temperature, adding an acid to decompose the excess of metal hydride, adding water thereto and collecting the precipitated product. The recovery may be also accomplished by shaking the reaction mixture with a suitable solvent, eliminating the solvent from the resultant extract and recrystallizing the product from any appropriate solvent.

In Step [3], the hydrolysis of the amide-alcohol (III) may be carried out under an acidic or a basic condition. The use of an acid is usually preferred, because not only does the ring closure yield the lactone (IV) but also the formation of the salt of the optically active primary amine with the acid takes place, the latter being advantageous in connection with the easy recovery of the reagent. Examples of the acid are inorganic acids such as hydrochloric acid and hydrobromic acid and organic acids such as acetic acid and formic acid.

In Step [4], the conversion of the lactone (IV) into the thiolactone (V) can be accomplished with ease by the use of an appropriate thiolactonating agent such as the combination of an alkali metal hydrosulfide and carbon disulfide or the combination of phosphorus pentasulfide and imidazole.

As one of the typical procedures for the conversion, an alkali hydrosulfide (e.g. sodium hydrosulfide, potassium hydrosulfide) is dissolved in a polar solvent (e.g. N,N-dimethylformamide, N,N-dimethylacetamide, tetramethylurea, hexamethylphosphoric triamide, sulfolane) and, after drying over anhydrous sodium sulfate, anhydrous magnesium sulfate or molecular sieve, carbon disulfide is added thereto in an equimolar amount or a slightly excess amount with respect to the alkali hydrosulfide at room temperature. Then, the lactone (IV) is added, and the mixture is heated at 100° to 150°C for several hours. After the reaction is over, a dilute acid such as dilute hydrochloric acid is added to the reaction mixture, and the resulting mixture is extracted with a suitable solvent (e.g. ethyl acetate, toluene). The extract is washed with water or dilute acid, dried over anhydrous magnesium sulfate or the like and concentrated. The obtained residue is treated with a suitable solvent such as ether or n-hexane to give the thiolactone (V) in a high yield. Alternatively, the said extract may be treated with dilute hydrochloric acid and zinc powder or acetic acid and zinc powder for a short period of time so that the thiolactone (V) is obtained in a better yield and a higher purity.

In case of using the thiolactonating agent consisting of phosphorus pentasulfide and imidazole, the following procedure is favorably employed: the lactone (IV) and imidazole (or 2-methylimidazole) are dissolved in an appropriate solvent (e.g. sulfolane, pyridine, α-picoline); a tertiary amine (e.g. triethylamine, tri-tertiary butylamine) and phosphorus pentasulfide are added thereto; the resulting mixture is stirred at room temperature for a few hours and then refluxed at about 100°C for 20 to 50 hours; and the reaction mixture is treated as in the case of using the thiolactonating agent consisting of the alkali hydrosulfide and carbon disulfide. The thiolactone (V) is obtained in a good yield and a high purity.

The following examples are given to illustrate the present invention more precisely, but it is not intended to limit the present invention to these examples.

EXAMPLE 1

A mixture of cis-1,3-dibenzyl-2-oxo-imidazolidine-4,5-dicarboxylic acid (50.0 g), (R)-1-phenethylamine (17.9 g) and toluene (200 ml) is stirred and refluxed for 15 minutes. After the toluene is removed, the mixture is heated at 220 to 240°C for an hour. Ethanol (600 ml) is added to the residue to dissolve the reaction product. After the solution is cooled in an ice bath, the precipitate is filtered and washed with ethanol (200 ml) to give 50.2 g (81 %) of cis-1,3-dibenzyl-5-[(R)-1-phenethyl]-hexahydropyrro[3,4-d]imidazole-2,4,6-trione. M.P. 157° to 159°C. $[\alpha]_D^{20}$ + 48.0° (C = 2 in $CHCl_3$). IR (Nujol) 1780, 1705, 1680 $cm^{-1}$ (C = 0).

EXAMPLE 2

A mixture of the anhydride of cis-1,3-dibenzyl-2-oxo-imidazolidine-4,5-dicarboxylic acid (30.0 g), (R)-1-phenethylamine (11.36 g) and toluene (90 ml) is stirred and warmed at 60° to 65°C for 1 hour. The reaction mixture is cooled and the precipitate is filtered to give cis-1,3-dibenzyl-4-[N-(R)-1-phenethylcarbamoyl]-5-carboxy-2-oxo-imidazoline (34.6 g, 84.7 %). M.P. 193° to 194°C. IR (Nujol) 3320 $cm^{-1}$ (NH); 1738, 1655 $cm^{-1}$ (C = 0). This product (25.0 g) is heated and fused at 220° to 240°C for 1 hour. The residue is recrystallized from ethanol (300 ml) to yield cis-1,3-dibenzyl-5-[(R)-1-phenethyl]-hexahydropyrro[3,4-d]imidazole-2,4,6-trione (21.0 g, 87.4 %). M.P. 157° to 159°C. $[\alpha]_D^{24.5}$ + 48.8° (C = 1 in $CHCl_3$). IR (Nujol) 1780, 1705, 1680 $cm^{-1}$ (C = 0).

EXAMPLE 3

To a solution of the trione (65.5 g) prepared in Example 1 in ethanol (500 ml), 23.3 g of 97% sodium borohydride are added below room temperature. The mixture is stirred at room temperature for 15 hours. After the reaction is over, the mixture is neutralized by the addition of acetic acid (35 ml) and concentrated in vacuo. A suspension of the residue in water (500 ml) is stirred for 1.5 hours. The reaction product is filtered and washed with water (200 ml) and ether (150 ml) to yield cis-1,3-dibenzyl-4-[N-(R)-1-phenethylcarbamoyl]-5-hydroxymethyl-tetrahydroimidazol-2-one (64.1 g, 97%). M.P. 121° to 123°C. $[\alpha]_D^{25} + 25.6°$ (C = 1 in CHCl$_3$). IR (Nujol) 3450, 3300 cm$^{-1}$ (OH and NH); 1680, 1650 cm$^{-1}$ (C = 0). This product (10.0 g) is recrystallized twice from a mixture of isopropanol (70 ml) and water (20 ml) to afford the optically pure sample (5.0 g). $[\alpha]_D^{25} -9.6°$ (C = 2 in CHCl$_3$).

EXAMPLE 4

To a solution of cis-1,3-dibenzyl-5-[(R)-1-phenethyl]-hexahydropyrro[3,4-d]imidazole-2,4,6-trione (20.0 g) in methanol (200 ml), 97% sodium borohydride (3.55 g) is added with ice cooling. The resulting mixture is stirred at room temperature for 7 hours and neutralized by the addition of acetic acid (10 ml). Water (200 ml) is added to the mixture and the precipitate is filtered to give cis-1,3-dibenzyl-5-[(R)-1-phenethyl]-6-hydroxy-hexahydropyrro[3,4-d]imidiazole-2,4-dione (6.0 g, 3.%). M.P. 170°C. $[\alpha]_D^{20} + 58.0°$ (C = 1 in CHCl$_3$). IR (Nujol) 3350 cm$^{-1}$ (OH); 1690 to 1670 cm$^{-1}$ (C = 0). On the other hand, the filtrate is concentrated in vacuo, water (200 ml) is added to the residue, and the reaction product is extracted with chloroform (300 ml). The chloroform extract is washed with water, dried over anhydrous magnesium sulfate, and evaporated to dryness. The residual oil is fractionated by column chromatography on silica gel (150 g) using benzene-ethyl acetate (1:1) as a solvent to give cis-1,3-dibenzyl-5-[(R)-1-phenethyl]-6-hydroxy-hexahydropyrro[3,4-d]imidazol-2,4-dione (5.3 g, 26%) and cis-1,3-dibenzyl-4-[N-(R)-1-phenethylcarbamoyl]-5-hydroxymethyl-tetrahydroimidazol-2-one (6.9 g, 34%). M.P. 114° to 116°C. The preferred spectra of both samples are identified with those of the authentic samples.

To a solution of the dione (10.0 g) prepared in the preceding experiment in methanol (100 ml) cooled in an ice bath, sodium borohydride (3.75 g) is added. The resulting mixture is stirred at room temperature for 15 hours. The reaction mixture is neutralized by the addition of acetic acid (10 ml) and diluted with water (150 ml). The precipitate is filtered to yield cis-1,3-dibenzyl-4-[-(R)-1-phenethylcarbamoyl]-5-hydroxymethyl-tetrahydroimidazole-2-one (9.5 g). M.P. 113° to 116°C. The infrared spectrum of the sample is identical with that of the authentic sample.

EXAMPLE 5

A mixture of cis-1,3-dibenzyl-4-[N-(R)-1-phenethylcarbamoyl]-5-hydroxymethyl-tetrahydroimidazol-2-one ($[\alpha]_D^{25} -9.6°$ (C = 2 in CHCl$_3$) (20.0 g), dioxane (250 ml) and 20 % sulfuric acid (150 g) is stirred and refluxed for 2 hours. The reaction mixture is concentrated to one third of the original volume and diluted with water (100 ml). The precipitate is collected by filtration to give cis-1,3-dibenzylhexahydrofuro[3,4-d]imidazole-2,4-dione (13.8 g, 95 %). M.P. 113° to 115°C. $[\alpha]_D^{20} + 59.5°$ (C = 2 in CHCl$_3$). IR (Nujol) 1775, 1690 to 1710 cm$^{-1}$ (C = 0).

EXAMPLE 6

A mixture of the anhydride of cis-1,3-dibenzyl-2-oxo-imidazolidine-4,5-dicarboxylic acid (50.0 g), (R)-1phenethylamine (18.9 g) and toluene (200 ml) is stirred and refluxed at 105° to 110°C for 2 hours. The toluene is distilled off, and the resulting residue is heated at 210° to 220°C for 1 hour. cis-1,3-Dibenzyl-5-[(R)-1-phenethyl]-hexahydropyrro[3,4-d]imidazole-2,4,6-trione left as the residue is dissolved in ethanol (750 ml), to which 97 % sodium borohydride (23.3 g) is added below 10°C. The mixture is stirred at room temperature for 16 hours. After the reduction is completed, the mixture is neutralized by the addition of acetic acid (35 ml) and concentrated in vacuo. The residue which contains cis-1,3-dibenzyl-4-[N-(R)-1-phenethylcarbamoyl]-5-hydroxymethyltetrahydroimidazol-2-one is heated under reflux with n butanol (500 ml) and 35 % hydrochloric acid (100 ml) for 2 hours. After the reaction is over, the mixture is cooled to room temperature. The n-butanol layer is separated, washed with water and concentrated in vacuo. The precipitate is collected by filtration to yield cis-1,3-dibenzyl-hexahydrofuro[3,4-d]imidazole-2,4-dione (44.6 g, 93.1 %). M.P. 96° to 101°C. $[\alpha]_D^{25} + 13.8°$ (C = 2 in CHCl$_3$). IR (Nujol) 1775, 1690 to 1700 cm$^{-1}$ (C = 0).

EXAMPLE 7

A mixture of the anhydride of cis-1,3-dibenzyl-2-oxo-imidazolidine-4,5-dicarboxylic acid (10.0 g), (+)-1-phenyl-2-(p-tolyl)ethylamine (7.55 g) and xylene (40 ml) is heated and molten at about 6°C. The reaction intermediate crystallizes at 120° to 130°C and melts at 160 to 170°C. The reaction is completed by heating at 240° to 250°C for 2 hours. The solution of the resulting residue in ethanol is decolorized by charcoal treatment and evaporated to dryness to give the viscous oil of cis-1,3-dibenzyl-5-[(+)-1-phenyl-2-(p-tolyl)-ethyl]-hexahydropyrro[3,4-d]imidazole-2,4,6-trione (17.5 g). IR (Nujol) 1790, 1700 to 1710 cm$^{-1}$ (C = 0).

EXAMPLE 8

To a solution of the trione (7.89 g) prepared in Example 7 in 95 % ethanol (50 ml), 97 % sodium borohydride (2.3 g) is added with ice cooling. The mixture is stirred at room temperature overnight, neutralized by the addition of 17.5 % hydrochloric acid and diluted with ice-water (50 ml). The precipitate is collected to give optically active cis-1,3-dibenzyl-4-{N-[(+)-1-phenyl-2-(p-tolyl)ethyl]carbamoyl}5-hydroxymethyl-tetrahyroimidazol-2-one (6.18 g). M.P. 124° to 125°C. $[\alpha]_D^{20} -33.8°$ (C = 1 in CHCl$_3$). IR (Nujol) 3400, 3280 cm$^{-1}$ (OH and NH); 1686, 1654 cm$^{-1}$ (C = 0).

EXAMPLE 9

A mixture of the amide-alcohol (3.0 g) prepared in Example 8, dioxane (30 ml) and 20 % sulfuric acid (20 ml) is refluxed with stirring for 1 hour. After the reaction is completed, the mixture is concentrated to one third of the original volume and diluted with water (50 ml). The precipitate is filtered to give cis-1,3-dibenzyl-hexahydrofuro[3,4-d]imidazole-2,4-dione (1.53 g, 84.5 %). M.P. 106.5° to 109°C. $[\alpha]_D^{20} + 2.6°$ (C = 2 in CHCl$_3$). The infrared spectrum of the sample is identified with that of the authentic sample.

EXAMPLE 10

A mixture of 15.7 g of the anhydride of cis-1,3-dibenzyl-2-oxo-imidazolidine-4,5-dicarboxylic acid, 8.4 g of (+)-1-(2-naphthyl)ethylamine ($[\alpha]_D^{20} + 26.2°$) and 100 ml of toluene is stirred and refluxed for 1 hour. After the toluene is distilled off, the residue is heated at about 210°C for 1 hour. The crystalline residue is recrystallized from 800 ml of ethanol, yielding 20.17 g (88 %) of cis-1,3-dibenzyl-5-[(+)-1-(2-naphthyl)e- thyl]-hexahydro-pyrro[3,4-d]imidazole-2,4,6-trione. M.P. 174° to 175°C. $[\alpha]_D^{20}$ + 82.5° (C = 2 in CHCl$_3$). IR (Nujol) 1780, 1705, 1680 cm$^{-1}$ (C = 0).

EXAMPLE 11

A suspension of 5.0 g of the trione prepared in Example 10 in 90 ml of ethanol is cooled to −5°C, and 1.55 g of sodium borohydride are added. The mixture is kept at −5° to 6°C for 22 hours, at 6° to 11°C for 20 hours and then at room temperature for 3 days. After the reaction is completed, the mixture is neutralized to pH 6 to 7 by the addition of acetic acid and then diluted with 200 ml of water. The precipitate is filtered off, and washed with water. There are obtained 4.75 g (94.3 %) of cis-1,3-dibenzyl-4-{N-[(+)-1-(2-naphthyl)ethyl]carbamoyl}-5-hydroxymethyl-tetrahydroimidazol-2-one. M.P. 170° to 175°C. $[\alpha]_D^{20}$ + 49.5° (C = 2 in CHCl$_3$). IR (Nujol) 3350, 3310, 3270 cm$^{-1}$ (OH and NH); 1670, 1645 cm$^{-1}$ (C = 0).

EXAMPLE 12

A mixture of 4.0 g of the tetrahydroimidazol-2-one prepared in Example 11, 50 ml of dioxane and 30.0 g of 20 % sulfuric acid is stirred and refluxed for 2 hours. The mixture is concentrated to one third of the original volume in vacuo and diluted with 100 ml of water. The precipitate is collected by filtration to give 1.26 g (96.5 %) of optically active (+)-cis-1,3-dibenzyl-hexahydrofuro[3,4-d]imidazole-2,4-dione. M.P. 106 to 109°C. $[\alpha]_D^{20}$ + 16.0° (C = 2 in CHCl$_3$). The infrared spectrum of the sample is identical with that of the authentic sample.

EXAMPLE 13

A mixture of cis-1,3-dibenzyl-2-oxo-imidazolidine-4,5dicarboxylic acid (6.10 g), (+)-1-(2-thienyl)ethylamine ($[\alpha]_D^{22}$ + 6.46° (C = 2 in CHCl$_3$)) (2.30 g) and toluene (50 ml) is refluxed with stirring for 30 minutes. The toluene is distilled off, and the residue is heated at about 200°C. The resulting residue is recrystallized from ethanol to give cis-1,3-dibenzyl-5-[1-(2-thienyl)ethyl]-hexahydropyrro[3,4-d]-imidazole-2,4,6-trione (6.64 g, 87 %). M.P. 143° to 146°C. $[\alpha]_D^{20}$ + 34.0° (C = 2 in CHCl$_3$). IR (Nujol) 1780, 1710, 1680 cm$^{-1}$ (C = 0).

EXAMPLE 14

A mixture of cis-1,3-dibenzyl-4-{N-[1-(2-thienylethyl]carbamoyl}-5-carboxy-2-oxo-imidazolidine (25.0 g) and toluene (200 ml) is placed in a flask equipped with a water separator and refluxed for 15 hours, while the water is removed from the reaction mixture. The toluene is evaporated, and the crystalline residue is recrystallized from ethanol to give the same trione (20.5 g, 85.3 %) as prepared in Example 13. M.P. 143° to 146°C.

EXAMPLE 15

Sodium borohydride (2.69 g) is added to a suspension of the trione (7.66 g) prepared in Example 13 in ethanol (100 ml) in an ice bath. The mixture is stirred at 0° to 5°C for 4 hours and at 20° to 25°C for 21 hours. The reaction mixture is neutralized by the addition of acetic acid (6 ml) and diluted with water (1 liter). The precipitate is filtered to give cis-1,3-dibenzyl-4-{N-[1-(2-thienyl)ethyl]-carbamoyl}-5-hydroxy-tetrahyroimidazol-2-one (7.0 g, 90.6 %). M.P. 108° to 129°C. $[\alpha]_D^{20}$ + 17.7° (C = 2 in CHCl$_3$). IR (Nujol) 3400, 3240 cm$^{-1}$ (OH and NH); 1670, 1640 cm$^{-1}$ (C = 0).

EXAMPLE 16

A mixture of the amide-alcohol (2.0 g) prepared in Example 15, dioxane (50 ml) and 20 % sulfuric acid (30.0 g) is refluxed with stirring at 88° to 89°C for 1 hour. The reaction mixture is concentrated to one third of the original volume, diluted with water (50 ml) and cooled in an ice bath. The precipitate is collected by filtration to yield cis-1,3-dibenzyl-hexahyrofuro[3,4-d]imidazole-2,4-dione (1.36 g, 95 %). M.P. 100° to 103°C. $[\alpha]_D^{20}$ + 16.4° (C = 2 in CHCl$_3$). The infrared spectrum of the sample is identified with that of the authentic sample.

EXAMPLE 17

A mixture of cis-1,3-dibenzyl-2-oxo-imidazolidine-4,5-dicarboxylic acid (50.0 a), (1S, 2S)-(+)-threo-1-(p-nitrophenyl)-2-amino-1,3-propanediol (29.88 g), toluene (560 ml) and pyridine (130 ml) is stirred and refluxed for 15 hours. The toluene is distilled until 5 ml of water is separated from the distillate (3 hrs.). After the mixture is concentrated in vacuo, 76.40 g of the residue are recrystallized from 95 % ethanol to give cis-1,3-dibenzyl-5-[(1S, 2S)-(+)-threo-1-hydromethyl-2-(p-nitrophenyl)-2-hydroxyethyl]-hexahydropyrro[3,4-d]imidazole-2,4,6-trione (59.94 g, 80 %). M.P. 200° to 202°C. $[\alpha]_D^{21}$ + 28.0°C (C = 2 in N,N-dimethylformamide). IR (Nujol) 1780, 1720 to 1675 cm$^{-1}$ (C = 0); 1530, 1350 cm$^{-1}$ (NO$_2$).

EXAMPLE 18

To a suspension of the trione (59.0 g) prepared in Example 17 in 95 % ethanol (560 ml), sodium borohydride (16.87 g) is added below 5°C. The resulting mixture is stirred at room temperature for 4 days. The mixture is neutralized by the addition of acetic acid (33 ml), concentrated in vacuo below 60°C, and ethyl acetate (560 ml) and water (450 ml) are added to the residue. The ethyl acetate layer is separated and concentrated in vacuo. When the residual oil (55.83 g) is triturated with isopropanol (170 ml), crystallization takes place immediately. The product is filtered off to give 37.35 g (62.7 %) of cis-1,3-dibenzyl-4-{N-[(1S, 2S)-(+)-threo-1-hydroxymethyl-2-(p-nitrophenyl)-2-hydroxyethyl]carbamoyl}-5-hydroxymethyl-tetrahydroimidazol-2-one. M.P. 181.5° to 183°C. $[\alpha]_D^{20}$ + 18.20° (C = 2 in N,N-dimethylformamide). IR (Nujol) 3,450 to 3,240 cm$^{-1}$ (OH and NH); 1,685 to 1,645 cm$^{-1}$ (C = 0); 1540, 1350 cm$^{-1}$ (NO$_2$).

EXAMPLE 19

In an ice bath, sodium borohydride (16.87 g) is added to a suspension of the trione (59.0 g) prepared in Example 17 in 95 % ethanol (600 ml). The mixture is stirred at room temperature for 4 days. The reaction mixture is neutralized by the addition of acetic acid (33 ml), concentrated in vacuo below 60°C, and ethyl acetate (560 ml) and water (450 ml) are added to the residue. The ethyl acetate layer is separated and concentrated in vacuo to give the residual oil (58.3 g) of cis-1,3-dibenzyl-4-{N-[(1S, 2S)-(+)-threo-1-hydroxymethyl-2-(p-nitrophenyl)-2-hydroxyethyl]carbamoyl}-5-hydroxymethyltetrahydroimidazol-2-one. A mixture of the oily product and 17.5 % hydrochloric acid (280 ml) is refluxed with stirring for 2 hours. The reaction mixture is cooled below 5°C for 1 hour, and the precipitate is filtered to give cis-1,3-dibenzyl-hexahydrofuro[3,4-d]imidazole-2,4-dione (30.0 g, 84 %). M.P. 98° to 100°C. $[\alpha]_D^{20} + 44.1°$ (C = 2 in CHCl$_3$). The infrared spectrum of the sample is identified with that of the authentic sample.

EXAMPLE 20

A mixture of the amide-alcohol prepared in Example ($[\alpha]_D^{20} + 18.2°$ (C = 2 in N,N-dimethylformamide)) (50.0 g) and 17.5 % hydrochloric acid (250 ml) is stirred and refluxed for 2 hours. The reaction mixture is cooled below 5°C for 1 hour, and the precipitate is filtered to give cis-1,3-dibenzyl-hexahydrofuro[3,4-d]imidazole-2,4-dione (29.5 g, 97.8 %). M.P. 115° to 116°C. $[\alpha]_D^{20} + 59.2°$ (C = 2 in CHCl$_3$). IR (Nujol) 1775, 1700 cm$^{-1}$ (C = 0).

EXAMPLE 21

A mixture of cis-1,3-dibenzyl-2-oxo-imidazolidine-4,5-dicarboxylic acid (50.0 g), (1S, 2S)-(+)-threo-1-(p-methylsulfonylphenyl)-2-amino-1,3-propanediol (34.59 g) and dioxane (800 ml) is stirred and refluxed at 101° to 102°C for 15 hours. The reaction mixture is concentrated in vacuo to afford a viscous residue of cis-1,3-dibenzyl-5-[(1S,2S)-(+)-threo-1-hydroxymethyl-2-(p-methylsulfonylphenyl)-2-hydroxyethyl]-hexahydropyrro[3,4-d]imidazole-2,4,6-trione (79.35 g, 99.7 %). $[\alpha]_D^{21} + 29.0°$ (C = 2.0 in N,N-dimethylformamide). IR (liquid film) 1775, 1710 to 1670 cm$^{-1}$ (C = 0).

EXAMPLE 22

To a suspension of cis-1,3-dibenzyl-5-[(1S, 2S)-(+)-threo-1-hydroxyethyl]-hexahydropyrro[3,4-d]imidazole-2,4,6-trione (78.2 g) in 95 % ethanol, 97 % sodium borohydride (35.7 g) is added. The mixture is stirred at room temperature for 4 days. By the same workup of the reaction as described in Example 18, cis-1,3-dibenzyl-4-{N-[(1S, 2S)-(+)-threo-1-hydroxymethyl-2-(p-methylsulfonylphenyl)2-(hydroxy)ethylcarbamoyl}-5-hydroxymethyl-tetrahydroimidazol-2-one is obtained (47.92 g, 61 %). M.P. 138.5° to 140.5°C. $[\alpha]_D^{20} + 6.0°$ (C = 2 in methanol). IR (liquid film) 3340 to 3300 cm$^{-1}$ (OH and NH); 1665, 1642 cm$^{-1}$ (C = 0).

EXAMPLE 23 cis-1,3-Dibenzyl-4-{N-[(1S, 2S)-(+)-threo-1-hydroxymethyl-2-(p-methylsulfonylphenyl)-2-hydroxyethyl]carbamoyl}-5-hydroxymethyl-tetrahydroimidazol-2-one ($[\alpha]_D^{20} + 6.0°$ (C = 2 in methanol)) (50.0 g) is added to 17.5 % hydrochloric acid (250 ml) and the mixture is refluxed for 2 hours. By the same workup of the reaction as described in Example 20, cis-1,3-dibenzyl-hexahydrofuro[3,4-d]imidazole-2,4-dione is obtained (26.93 g, 95 %). M.P. 115° to 116°C. $[\alpha]_D^{20} + 59.8°$ (C = 2 in CHCl$_3$). The infrared spectrum of this sample is identified with that of the authentic sample.

EXAMPLE 24

A mixture of cis-1,3-dibenzyl-2-oxo-imidazolidine-4,5-dicarboxylic acid anhydride (50.5 g), (S)-phenylaninol (22.65 g) and dioxane (750 ml) is stirred and refluxed at 101° to 102°C for 24 hours. Concentration in vacuo gives a semi-crystalline mass, which is recrystallized from 66 % ethanol (250 ml) to afford a cis-1,3-dibenzyl-5-[(S)-(1-benzyl-2-hydroxyethyl)]-hexahydropyrro[3,4-d]imidazole-2,4,6-trione (54.0 g, 77 %). M.P. 139° to 141°C. $[\alpha]_D^{21} - 61.0°$ (C = 1.0 in N,N-dimethylformamide). IR (liquid film) 1770, 1700, 1650 cm$^{-1}$ (C = 0).

EXAMPLE 25

To a suspension of cis-1,3-dibenzyl-5-[(S)-(1-benzyl-2-hydroxyethyl)]-hexahydropyrro[3,4-d]imidazole-2,4,6-trione (50.0 g) in 95 % ethanol (500 ml), 97 % sodium borohydride (16.1 g) is added. The reaction mixture is stirred at room temperature for 4 days. By the same workup of the reaction as described in Example 18, cis-1,3-dibenzyl-4-[N-(S)-1-benzyl-2-hydroxyethylcarbamoyl]-5-hydroxymethyl-tetrahydroimidazol-2-one is obtained (26.9 g, 53.4 %). M.P. 142.5° to 145°C. IR (liquid film) 3300 cm$^{-1}$ (OH and NH); 1695, 1655 cm$^{-1}$ (C = 0).

EXAMPLE 26

A mixture of cis-1,3-dibenzyl-4-[N-(S)-1-benzyl-2-hydroxyethylcarbamoyl]-5-hydroxymethyl-tetrahydroimidazol-2-one (50.0 g), dioxane (200 ml) and 20 % sulfuric acid (200 ml) is stirred and refluxed for 1 hour. The reaction mixture is poured on ice and extracted with ethyl acetate. The ethyl acetate layer is washed with water and concentrated in vacuo to give a semi-crystalline mass (33.43 g). This is crystallized from ether to afford cis-1,3-dibenzyl-hexahydrofuro[3,4-d]imidazole-2,4-dione (28.89 g, 84.8 %). M.P. 103° to 104°C. $[\alpha]_D^{20} + 14.0°$ (C = 2.0 in CHCl$_3$). The infrared spectrum of this sample is identified with that of the authentic sample.

EXAMPLE 27

A mixture of cis-1,3-dibenzyl-2-oxo-imidazolidine-4,5-dicarboxylic acid (50.0 g), (S)-phenylalanine (23.47 g) and toluene (200 ml) is refluxed with stirring for 30 minutes. The toluene is distilled off, and the resulting residue is heated at 200° to 230°C for 1 hour. The reaction residue is recrystallized from 84 % ethanol (400 ml) to give cis-1,3-dibenzyl-5-{(S)-[1-carboxy-2-phenyl]ethyl}-hexahydropyrro[3,4-d]imidazole-2,4,6-trione (61.3 g, 90 %). M.P. 146° to 147°C. IR (Nujol) 1790, 1740, 1710, 1670 cm$^{-1}$ (C = 0).

EXAMPLE 28

To a suspension of the trione (60.0 g) prepared in Example 27 in 95 % ethanol (600 ml), 97 % sodium borohydride (18.78 g) is added below room temperature. The mixture is stirred at room temperature for 15 hours. The reaction mixture is neutralized by the addition of acetic acid (60 ml) and diluted with ice water (1,200 ml). The precipitate is filtered to give cis-1,3-dibenzyl-4-[N-(S)-1-carboxy-2-phenethylcarbamoyl]-5-hydroxymethyl-tetrahydroimidazol-2-one (47.4 g, 78.3 %). M.P. 131° to 132°C. IR (Nujol) 3410, 3270 cm$^{-1}$ (OH and NH); 1735, 1680, 1655 cm$^{-1}$ (C = 0).

EXAMPLE 29

A mixture of the amide-alcohol (50.0 g) prepared in Example 28, dioxane (200 ml) and 20 % sulfuric acid (200 ml) is refluxed with stirring for 1 hour. To the reaction mixture, ice water is added, the reaction product is extracted with ethyl acetate and the organic layer is concentrated in vacuo. The residue is triturated with ether and the crystalline product is filtered to yield cis-1,3-dibenzyl-hexahydrofuro[3,4-d]imidazole-2,4- dione (30.0 g, 90.2 %). M.P. 111° to 112°C. $[\alpha]_D^{21}$ + 5.8° (C = 2 in CHCl$_3$). The infrared spectrum of the sample is identified with that of the authentic sample.

EXAMPLE 30

A solution of 70 % sodium hydrosulfide (technical grade, 7.5 g) in 150 ml of N,N-dimethylacetamide is dried over anhydrous sodium sulfate (21 g) by stirring it for 6 hours and standing overnight. Carbon disulfide (7.5 ml) is added to the solution, the resulting mixture is stirred for about 30 minutes at room temperature, followed by the addition of 10.0 g of cis-1,3-dibenzyl-hexahydrofuro[3,4-d]imidazole-2,4-dione ($[\alpha]_D^{20}$ + 62° (C = 2 in CHCl$_3$)). The mixture is stirred and heated at 110°C for 4 hours. After the reaction is over, the mixture is acidified by the addition of 12 % hydrochloric acid (300 ml), and the reaction product is extracted with 200 ml of ethyl acetate. The ethyl acetate extract is washed with water, dried over anhydrous sodium sulfate and evaporated to dryness. The residue (about 11 g) is triturated with 50 ml of ether, and the precipitate is filtered to give cis-1,3-dibenzyl-hexahydrothieno[3,4-d]imidazole-2,4-dione (9.60 g, 91.5 %). M.P. 121° to 123°C. $[\alpha]_D^{20}$ + 86° (C = 1 in CHCl$_3$). IR (Nujol) 1700, 1680 cm$^{-1}$ (C = 0).

EXAMPLE 31

A solution of 70 % sodium hydrosulfide (technical grade, 7.5 g) in 160 ml of N,N-dimethylacetamide is dried over anhydrous magnesium sulfate (18 g) by stirring for 5 hours and standing overnight at room temperature. Carbon disulfide (7.5 ml) is added to the solution, and the resulting mixture is stirred at room temperature for about 30 minutes, followed by the addition of 10.0 g of cis-1,3-dibenzyl-hexanhydrofuro[3,4-d]imidazole-2,4-dione ($[\alpha]_D^{20}$ + 62° (C = 2 in CHCl$_3$)). The mixture is heated with stirring at 110°C for 4 hours. The reaction mixture is acidified by the addition of 12 % hydrochloric acid (300 ml), and the reaction product is extracted with 200 ml of ethyl acetate. The organic layer is washed with water and concentrated in vacuo. The resulting residue is dissolved in 200 ml of toluene, followed by the addition of 7 % hydrochloric acid (100 ml) and zinc powder (10 g) into the solution. The mixture is stirred and warmed at 60° to 65°C for 2 hours. The reaction mixture is cooled to room temperature and filtered, and the precipitate on the funnel is washed with toluene. The toluene layer is separated, washed with water and evaporated to dryness, yielding 10.44 g (99.5 %) of cis-1,3-dibenzyl-hexahydrothieno[3,4-d]imidazole-2,4-dione as the crystalline residue. The infrared spectrum of the residue is identical in all respects with that of the optically pure sample prepared by recrystallization. The residue (10.44 g) is recrystallized from aqueous methanol to give 8.41 g (80 %) of the optically pure sample. M.P. 123° to 125°C. $[\alpha]_D^{20}$ + 91.0° (C = 1 in CHCl$_3$). IR (Nujol) 1700, 1680 cm$^{-1}$ (C = 0).

EXAMPLE 32

Carbon disulfide (7.5 ml) is added with stirring to a solution of potassium hydrosulfide in N,N-dimethylacetamide (this solution being prepared by saturating a mixture of potassium hydroxide (5.2 g) and 150 ml of N,N-dimethylacetamide with hydrogen sulfide and drying over 21 g of anhydrous sodium sulfate.). cis-1,3-Dibenzyl-hexahydrofuro[3,4-d]imidazole-2,4-dione (10.0 g) is added to the solution, and the mixture is stirred and heated at 110°C for 5 hours. The reaction mixture is acidified by the addition of 21 % hydrochloric acid (200 ml), and the reaction product is extracted with 200 ml of toluene. The organic layer is washed with water and evaporated to dryness. The residue is triturated with a mixture of methanol (30 ml) and water (10 ml), and the precipitate is collected by filtration to give cis-1,3-dibenzyl-hexahydrothieno[3,4-d]imidazole-2,4-dione (8.5 g, 81 %). M.P. 122 ° to 124°C. $[\alpha]_D^{20}$ + 90° (C = 1 in CHCl$_3$). The infrared spectrum of the sample is identical with that of the authentic sample.

EXAMPLE 33

To a solution of cis-1,3-dibenzyl-hexahydrofuro[3,4-d]imidazole-2,4-dione (10.0 g) and imidazole (10.5 g) in 100 ml of sulfolane, triethylamine (60 ml) and phosphorus pentasulfide (20.6 g) are added. The mixture is stirred at room temperature for 1 hour and then refluxed at 95° to 100°C for 40 hours. After the reaction is over, 300 ml of toluene and Celite-535 (5 g) are added to the reaction mixture cooled in an ice water bath, followed by addition of 18 % hydrochloric acid and filtration of the resulting mixture. The organic layer is washed with water and dilute acid and concentrated in vacuo to give the residual oil (11.5 g). The residue is triturated with a mixture of ether and petroleum ether, and the precipitate is filtered to give cis-1,3-dibenzyl-hexahydrothieno[3,4-d]imidazole-2,4-dione (8.5 g, 81 %). M.P. 121° to 123°C. $[\alpha]_D^{20}$ + 85° (C = 1 in CHCl$_3$). The infrared spectrum of the sample is identical with that of the authentic sample.

EXAMPLE 34

Triethylamine (300 ml) and phosphorus pentasulfide (41 g) are added to a solution of 10.0 g of cis-1,3-dibenzylhexahydrofuro[3,4-d]imidazole-2,4-dione ($[\alpha]_D^{20}$ + 62° (C = 2 in CHCl$_3$)) and imidazole (21 g) in 150 ml of α-picoline. The mixture is stirred at room temperature for 1 hour and refluxed at about 100°C for 48 hours. Ethyl acetate (300 ml) and Celite-535 (5 g) are added to the reaction mixture cooled in an ice water bath, followed by addition of water (150 ml) and a saturated solution of sodium chloride (100 ml) and filtration of the resulting mixture. The organic layer is washed with water and concentrated in vacuo. The resulting residue is dissolved in 200 ml of toluene, followed by the addition of 7 % hydrochloric acid (100 ml) and zinc powder (10 g). The mixture is stirred and warmed at 60° to 65°C for 2 hours. The reaction mixture is cooled to room temperature and filtered off. The toluene layer is washed with water and concentrated in vacuo. The residue is triturated with ether, and the precipitate is filtered to give cis-1,3-dibenzyl-hexahydrothieno[3,4-d]imidazole-2,4-dione (8.9 g, 85 %). M.P. 124° to 126°C. $[\alpha]_D^{20}$ + 86° (C = 2 in CHCl$_3$).

EXAMPLE 35

To a Grignard reagent solution prepared from 3-ethoxypropyl bromide (41.7 g), magnesium metal (shoot, 11.2 g) and iodine (0.2 g) in 110 ml of anhydrous ether and 30 ml of anhydrous benzene, a solution of cis-1,3-dibenzyl-hexahydrothieno[3,4-d]imidazole-2,4-dione ($[\alpha]_D^{20}$ + 91°, 60.0 g) in 700 ml of anhydrous benzene is added with stirring for two and half hours at 25° to 40°C. The mixture is stirred and refluxed at 68° to 73°C for 5 hours. The reaction mixture is decomposed by the addition of 3N sulfuric acid (280 g) below 20° C. The organic layer is washed with water and concentrated in vacuo to give the residual oil of 76 g of cis-1,3-dibenzyl-4-hydroxy-4-(3-ethoxypropyl)-hexahydrothieno[3,4-d]imidazol-2-one. $[\alpha]_D^{20} + 17°$ (C = 1 in CHCl$_3$). IR (Nujol) 3350 cm$^{-1}$ (OH); 1690 cm$^{-1}$ (C = O).

A mixture of cis-1,3-dibenzyl-4-hydroxy-4-(3-ethoxypropyl)-hexahydrothieno[3,4-d]imidazol-2-one (65.0 g.), 300 ml of toluene and 95 % sulfuric acid (1.0 g) is refluxed for 1.5 hours. The reaction mixture is cooled at room temperature and diluted with 200 ml of water. The toluene layer is washed with 10 % aqueous sodium carbonate solution, twice with water and concentrated in vacuo. The oily cis-1,3-dibenzyl-4-(3-ethoxypropylidene)-hexahydrothieno[3,4-d]imidazol-2-one (about 62 g) is dissolved in 600 ml of isopropanol and hydrogenated in the presence of 3.1 g of palladium oxide at room temperature and 15 to 20 atm. pressure for 1 hour. The catalyst is filtered off, and the solution is concentrated in vacuo. The oily cis-1,3-dibenzyl-4-(3-ethoxypropyl)-hexahydrothieno[3,4-d]-imidazol-2-one (about 62 g) is dissolved in a mixture of acetic acid (180 ml) and 35 % hydrochloric acid (210 ml). The resulting mixture is heated with stirring at 70° to 75°C for 3 hours. The reaction mixture is concentrated in vacuo, and a small amount of toluene is added to the residue and evaporated to dryness, until most of the acetic acid and hydrochloric acid is removed. To the resulting residue, 200 ml of toluene and 600 ml of water are added, and the mixture is decolorized with charcoal treatment. The aqueous layer is concentrated in vacuo, and the residue is triturated with 80 ml of acetone. The precipitate is filtered to give cis-1,3-dibenzyl-2-oxo-decahydroimidazo[4,5-c]thieno[1,2-a]thiolium chloride (51.2 g, 84 %). M.P. 138° to 139°C. $[\alpha]_D^{20} - 23°$ (C = 1 in methanol). IR (Nujol) 1710 to 1700 cm$^{-1}$ (C = O).

A mixture of the thiolium chloride (50.0 g) described above, 200 ml of anhydrous toluene and sodio-malonate prepared from diethylmalonate (140 g) and 98 % sodium methoxide (20.7 g) is stirred and refluxed (95° to 100°C) for 3 hours. The reaction mixture is acidified by the addition of a mixture of 95 % sulfuric acid (19.3 g) and 200 ml of water below 10°C. Toluene (200 ml) is further added to the resulting mixture, and the toluene layer is separated, washed with water and concentrated in vacuo to remove the toluene and the excess of diethyl malonate. The syrupy cis-1,3-dibenzyl-4-(4,4-dicarboxybutyl)-hexahydrothieno[3,4-d]imidazol-2-one (about 67 g) is dissolved in 540 ml of 47 % hydrobromic acid. The mixture is refluxed with stirring at 120° to 125°C for 10 hours. Toluene (210 ml) is added with stirring to the reaction mixture, and the toluene layer is separated. The aqueous layer is concentrated in vacuo (below 80°C), 30 ml of water and 60 ml of toluene are added to the residue and the mixture is neutralized by the addition of 20 % sodium hydroxide (75 ml). The resulting mixture is phosgenated by dropping therein a solution of 30 % phosgene in toluene (75 and 20 % sodium hydroxide (60 ml). The reaction mixture is acidified by the addition of 35 % hydrochloric acid (30 ml) below 20°C. The precipitate is collected by filtration to give 28.2 g (91 %) of the crude product which is recrystallized from water to yield 25.4 g (83.5 %) of pure d-biotin. M.P. 228° to 230°C. $[\alpha]_D^{20} + 91.0°$ (C = 1 in 0.1N sodium hydroxide). The infrared spectrum of the sample is identical with that of the authentic sample.

What is claimed is:
1. A process for producing an optically active (+)-thiolactone of the formula:

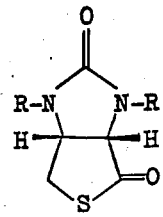

wherein R is a benzyl group, which comprises reacting a dicarboxylic acid of the formula:

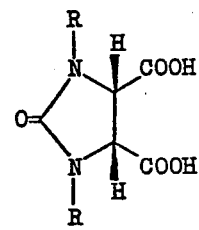

wherein R is as defined above or the acid anhydride, ester or halide thereof with an optically active primary amine of the formula:

R$^1$ — NH$_2$ where R$^1$ is an optically active primary amine residue, reducing the resultant trione of the formula:

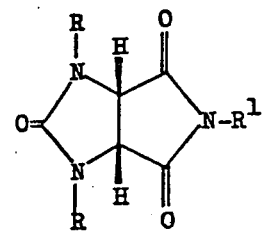

wherein R and R$^1$ are each as defined above, hydrolyzing the resulting amide-alcohol of the formula:

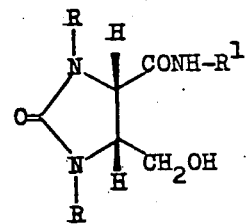

wherein R and R$^1$ are each defined above and treating the thus obtained lactone of the formula:

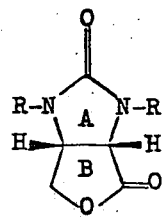

wherein R is as defined above with an alkali metal hydrosulfide and carbon disulfide or phosphorus pentasulfide and imidazole.

2. The process according to claim 1, wherein the thiolactonation is carried out using an alkali metal hydrosulfide and carbon disulfide.

3. The process according to claim 1, wherein the thiolactonation is carried out using phosphorus pentasulfide and imidazole.

4. The process according to claim 1, wherein the optically active primary amine is selected from the group consisting of (R)-1-phenethylamine, (1S,2S)-(+)-threo-1-(p-nitrophenyl)-2-amino-1,3-propanediol, (1S,2S)-(+)-threo-1-(p-methylsulfonylphenyl)-2-amino-1,3-propanediol, (+)-1-phenyl-2-(p-tolyl)ethylamine, (+)-1-(2-naphthyl)ethylamine, (+)-1-(2-thienyl)ethylamine, (S)-phenylalaninol and (S)-phenylalanine.

5. A compound of the formula:

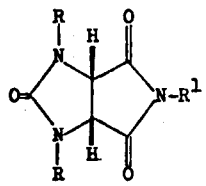

wherein R is a benzyl group and $R^1$ is an optically active primary amine residue.

6. The compound of claim 5, wherein the optically active primary amine is selected from the group consisting of (R)-1-phenethylamine, (1S,2S)-(+)-threo-1-(p-nitrophenyl)-2-amino-1,3-propanediol, (1S,2S)-(+)-threo-1-(p-methylsulfonylphenyl)-2-amino-1,3-propanediol, (+)-1-phenyl-2-(p-tolyl)ethylamine, (+)-1-(2-naphthyl)ethylamine, (+)-1-(2-thienyl)ethylamine, (S)-phenylalaninol and (S)-phenylalanine.

7. A compound of the formula:

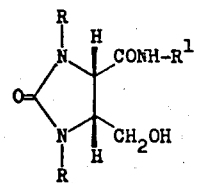

wherein R is a benzyl group and $R^1$ is an optically active primary amine residue.

8. The compound of claim 7, wherein the optically active primary amine is selected from the group consisting of (R)-1-phenethylamine, (1S,2S)-(+)-threo-1-(p-nitrophenyl)-2-amino-1,3-propanediol, (1S,2S)-(+)-threo-1-(p-methylsulfonylphenyl)-2-amino-1,3-propanediol, (+)-1-phenyl-2-(p-tolyl)ethylamine, (+)-1-(2-naphthyl)ethylamine, (+)-1-(2-thienyl)ethylamine, (S)-phenylalaninol and (S)-phenylalanine.

* * * * *